United States Patent [19]

Parker

[11] Patent Number: 5,267,862
[45] Date of Patent: Dec. 7, 1993

[54] INTRAORAL APPLIANCE

[76] Inventor: Jonathan A. Parker, 9635 29th Ave. N., Plymouth, Minn. 55441

[21] Appl. No.: 1,843

[22] Filed: Jan. 8, 1993

[51] Int. Cl.⁵ .......................... A61C 5/00; A61C 9/00; A61C 5/14; A61F 5/56
[52] U.S. Cl. .................................. 433/215; 433/214; 128/848; 128/859
[58] Field of Search .............. 433/214, 215; 128/848, 128/859, 861

[56] References Cited

U.S. PATENT DOCUMENTS

| | | |
|---|---|---|
| 587,358 | 8/1897 | Anderson . |
| 736,869 | 12/1903 | Moulton . |
| 1,674,336 | 6/1928 | King . |
| 2,424,533 | 7/1947 | Faires ..................... 128/136 |
| 2,574,623 | 11/1951 | Clyde ..................... 128/136 |
| 2,626,268 | 2/1953 | Leppich ..................... 128/136 |
| 2,705,006 | 3/1955 | Cettel et al. ..................... 128/136 |
| 3,132,647 | 5/1964 | Corniello ..................... 128/136 |
| 3,434,470 | 3/1969 | Strickland ..................... 128/136 |
| 3,478,742 | 11/1969 | Bohlmann ..................... 128/172.1 |
| 4,169,473 | 10/1979 | Samelson ..................... 128/136 |
| 4,196,724 | 4/1980 | Wirt et al. ..................... 128/136 |
| 4,715,368 | 12/1987 | George ..................... 128/136 |
| 5,003,994 | 4/1991 | Cook ..................... 128/848 |
| 5,018,533 | 5/1991 | Hawkins ..................... 128/848 |
| 5,056,534 | 10/1991 | Wright ..................... 128/848 |
| 5,103,838 | 4/1992 | Yousif ..................... 128/859 |

*Primary Examiner*—Gene Mancene
*Assistant Examiner*—Cindy A. Cherichetti
*Attorney, Agent, or Firm*—D. A. Jacobson

[57] ABSTRACT

Dental appliances formed using this method provide projections of the appliance itself which provide the necessary gripping forces rather than extraneous wires or other parts. The projections are formed by cutting grooves in casts of the teeth arches which will result in a projection, which will bear against the teeth, when the cast surface is duplicated in plastic. A first embodiment forms upper and lower plastic components, each having projections from the casts using the lost wax technique. These components are joined together in a predetermined relationship using a wax bite registration taken while the patient held his jaw in the predetermined relationship, and a dental articulator. A second method forms the plastic components directly over the casts. In this method the components are joined together, while mounted over the patient's arches, with the patient holding his jaw in the predetermined relationship. Both methods can be used to produce a single component with no joining of components then being required.

10 Claims, 8 Drawing Sheets

INTRAORAL APPLIANCE

FIELD OF THE INVENTION

This invention relates to the field of oral appliances and particularly to appliances held in place by projections which are part of the appliance itself instead of additional metal extensions or other apparatus.

BACKGROUND OF THE INVENTION

The following oral appliances utilize a variety of means to attach appliances within a patients mouth to correct a variety of medical conditions:

| Name of Inventor | U.S. Pat. No. |
| --- | --- |
| Anderson | |
| S. A. Moulton | 736,869 |
| E. J. King | 1,674,336 |
| W. J. Faires | 2,424,533 |
| M. Clyde | 2,574,623 |
| E. L. Leppich | 2,626,268 |
| L. L. Cetttel et al. | 2,705,006 |
| G. Corniello | 3,132,647 |
| J. C. Strickland | 3,434,470 |
| E. H. Bohlmann | 3,478,742 |
| C. F. Samelson | 4,169,473 |
| Wirt et al. | 4,196,724 |
| P. T. George | 4,715,368 |
| K. J. Toone | 4,901,737 |
| G. W. Cook | 5,003,994 |

Anderson uses an elastic band around the head to secure a generally cylindrical shaped appliance within the lips. Slots along the axis of the appliance reduces and controls the airflow into the mouth.

Moulton uses a flexible plate adapted to be held between the lips and in contact with the teeth, the plate having a check valve adapted to regulate the amount of air admitted to or expelled from the lungs through the mouth.

King uses a front plate member which has a curvature corresponding to the curvature of the upper and lower front teeth. The plate cooperates with a body portion which forms an upper interior channel to receive the upper front teeth of the user and to form a lower interior channel to receive the lower front teeth. These two channels are spaced apart which props the teeth apart so air may pass in and out freely. The member also moves the jawbone downward to provide a larger passage breathing.

Fairies uses a pair of frame members which are curved to correspond to the curvature of the teeth and sized to fit between the teeth and lips of the user. The frames are pivotably secured together at their ends. A spring is arranged to offset one frame from the other to expand the reach of the members to prevent air from being drawn in through the mouth to prevent snoring.

Clyde uses lower and upper semi-elliptical cylindrical plastic members adapted to fit in the entrance of the mouth to prevent snoring. The members are hinged together. The lower member fits between the lower lip and cheeks and the outer periphery of the lower jaw and the upper member fits between the lower lip and the cheeks. The members are held in an extended position by a light wire spring so the members will expend when the wearer's mouth opens. Supplemental air openings in the lower members are arranged to be covered when the device is closed and uncovered an amount which depends upon the amount the mouth is open.

Leppich uses a plate of flexible material which is shaped to fit in the mouth between the teeth and lips which has a bead around the periphery to prevent cutting into the mouth tissues.

Cettel et al teaches a molded plastic mouthpiece which has a T-shaped cross-section with the head of the T closing the mouth opening and with portions thereof seating between the upper and lower lips respectively and the gums of the upper and lower jaws. This retains the mouthpiece in position in the mouth and prevents the passage of air thereinto. The portion of the mouthpiece opposite the teeth have mating depressions to receive them. A reinforcing wire adds rigidity to the mouthpiece.

Corniello mounts a tongue depressing means in the patient's mouth. The mounting means attaches the tongue depressor to the upper jaw using a variety of mounting means depending upon the number of upper teeth or their absence. A depressor with projection adjusting means extends rearward and downward from the mounting means.

Strickland uses an oral device with a plate adapted to be placed within the mouth in the U-shaped space defined by the upper teeth. The plate releasably grips the upper teeth and reduces snoring by reducing the volume of air flow.

Bophlmann teaches a molded plastic support, guard and barrier device which is fitted between the teeth of a patient for tooth, lip and tongue positioning. The device has sockets to receive the upper and lower teeth and projection parts for lip positioning. Samelson teaches an integrally molded body with dental engaging arches and a rearward opening central socket for cooperating with the forward portion of the users tongue arranged to draw the tongue forward and increase the size of the breathing passage.

Wirt et al. uses a suction producing formation to apply suction to wedge the tip of the tongue within rearwardly converging walls of a receptacle arranged to seal against and maintain holding pressure on the tongue.

George uses a one piece dental mouthpiece with a front beak which houses an orifice airway. This is held in place by custom-fitting molar and labial wire clasps and guide.

Toone uses an oral cavity appliance that repositions the mandible open and protrusive by a suitably molded shape. the appliance is open across the front and preferably across the top with a lip extending over the labial surface of the mandibular incisors, over the lingual surfaces and downwardly into the lingual vestibule. This covers the palatial surfaces of the maxillary bicuspids and molars and extends onto the palate. The lack of full palatal coverage provides space for the tongue, which rests in its normal position. This reduces snoring and apneic episodes.

Cook has a rigid shell with an upper tray, and a cam structure which advances the mandible structure forward with respect to the maxilla structure, stops to hold the mouth open, and a soft resilient pliable socket inside of the tray. The pliable socket has tooth sockets for a plurality of upper teeth, and a gum socket for the maxilla gigva tissue to enable the pliable socket to conform to the users teeth to spread the loading.

None of these inventions utilize projections which are formed as a part of the appliance itself to grip the teeth and secure the appliance in place. Further, none of these inventions utilize a plastic which softens sufficiently within the mouth to eliminate pressure points between the appliance and the teeth without the necessity of a softer plastic liner.

SUMMARY OF THE INVENTION

This invention provides a means for attaching an oral appliance to the teeth using an extension of the appliance itself as the attachment means. The application illustrated here to correct sleep apnea is representative, since any other oral appliance held by the teeth is a candidate for this attachment means. This applicationced because of the large forces required to hold the jaw forward to correct the problem of sleep apnea, since a particularly secure grip is required. Because this application requires such a secure grip, any other appliance secured to the teeth requiring the same or a lesser attachment force is a candidate for this attachment means.

The appliance is made of plastic material and fits within the oral cavity between and over the upper and lower dental arches. For this application the appliance must hold the teeth spaced apart with the jaw projected downward and forward. The appliance is manufactured in two parts, an upper and lower component, which fit around the respective dental archs to near the gum line. These two components are attached together to form the appliance. The upper and lower components are secured together such that the jaw is held as required with a front breathing opening provided. The material used to form these two parts is plastic. The preferred plastic is Bruxeze, since this will soften sufficiently at body temperature to eliminate pressure points which may otherwise require a liner.

The appliance fits over both dental archs with both the upper and lower components being secured to its respective archs by projections of the plastic appliance itself which extend inward against two back teeth on the outer, or buccal side of the tooth, on both sides of the arch. For appliances where a different attachment force is required the number of projections or the particular teeth engaged can be changed. These projections extend inward parallel to the biting surfaces of the teeth and are positioned to engage a tooth between the gum tissue and the height of contour of the tooth. Since the height of contour of a tooth is the point of maximum extension, this will require the appliance to be slightly deformed to install or remove it. This deformation force provides the holding force for the appliance.

Two methods of making this appliance are described and both use conventional dental techniques and equipment. In both methods impressions of the upper and lower dental archs are made first using impression trays and conventional impression material.

Stone casts are then made using these impressions and conventional dental stone material which replicate both the upper and lower dental arch. Grooves are cut into two rear teeth replicas on both sides of both the upper and the lower stone casts. These grooves are positioned between the point of maximum extension of the respective tooth and its gum line, and are oriented parallel to the biting surfaces of the teeth.

In a first method, wax is then molded around both stone casts. Plastic part replicas of these wax molds are made using conventional dental lost wax techniques to produce separate upper and lower plastic replicas. These plastic part replicas will each have a projection directed inwardly from the outer (buccal) side of two rear teeth resulting from the grooves which were cut into the teeth replicas in the stone casts. As discussed earlier, these integral projections of the appliance itself, provided by this simple procedure, are the only means necessary to hold the appliance securely in place.

In this first method of manufacture, a bite registration is also taken of the patient in the conventional manner using heat softened wax with the jaw held in the position required to correct sleep apnea. This requires that the jaw be positioned forward approximately 60 to 75% of the patient's maximum ability to protrude the mandible, and held open 5 to 8 mm. more than the patient's normal biting position.

This wax bite registration is then used to mount the upper and lower casts on a dental articulator in the same relationship as the dental arches had when the registration was taken in the mouth. This relationship is established by the mounting of the stone casts with respect to the dental articulator, and the angle between the two casts, established by an adjustable guide pin, used to set the angle between the casts. The upper and lower plastic component replicas are placed over the respective upper and lower casts, which are held in the pre-established relationship by the dental articulator, and the plastic components are then secured together using an adhesive. With the upper and lower components being secured together in the same relationship as that determined by the wax bite registration, the resulting integral plastic appliance will hold the jaw in that relationship when placed over the dental arches in the patient's mouth.

In a second method of manufacture, the preparation of stone casts with a groove in two back teeth is the same, however the steps of preparing a wax bite registration, the use of a dental articulator, and the preparation of wax molds of the stone casts are omitted. Here the two components are prepared from the stone casts by molding plastic directly over the two stone casts. A number of plastics are available which are suitable for this purpose. These include both two-part polymerizing plastics as well as thermoplastics.

The resulting two components are then joined together in the patient's mouth while the patient holds his mouth in the desired relationship. The two components are then joined together using two wedge shaped plastic blocks placed between the components on both sides of the dental arch between the rear teeth. An adhesive is used to attach the wedge shaped blocks and two components together. As an alternative, the wedge shaped blocks can be thermoplastic or can be formed from a two-part polymerizing plastic to permit joining the two components together using the blocks themselves.

In both methods, the use of grooves cut into stone casts to produce a projection to hold the appliance in place is the same. Both methods also produce the same parts in the same sequence. The resulting appliances also have the same relationship between the parts. The second method has an advantage in that, since no laboratory equipment is required, the dentist can prepare the appliance in his own office. The accuracy of the relationship between the parts is less in the second method than in the first method however.

In both methods the parts are sized to fit exactly over the cast of the dental arch, consequently any grooves cut into the teeth replicas in the cast will result in a projection which will bear against the tooth. Experience in manufacturing this appliance should provide a groove depth with a resulting retentive force exactly that required to hold the appliance in place with no discomfort to the patient. If required however, since an excessive retentive force can cause soreness on the teeth or difficulty in seating the appliance, the projection can readily be reduced in the dental office using a dental handpiece and bur in a final fitting proecess. In this process, the appliance fit is tested in the mouth, a small amount of material is removed from the projection, and the fit of the appliance again tested in the mouth. This process is repeated until a secure but comfortable fit is obtained. Being able to reduce the amount the projection extends in this manner provides a simple means to change the retentive forces of the appliance after manufacture.

This application requires two components to hold the jaw in the necessary relationship to correct sleep apnea. This projection means can be used for an appliance attached to only one arch of teeth however. In this case, only one component would be manufactured using the same techniques and tools used in the preparation of two components, and the steps necessary to join two components together are simply omitted.

DETAILED DESCRIPTION OF THE PREFERRED METHOD OF CARRYING OUT THE INVENTION

The following descriptions illustrate the two methods of carrying out the invention. Both methods result in an essentially identical appliance, one method however can be performed in the dental office, while the other requires the services of a laboratory. These descriptions are given as illustrations and not as limitations.

Figure 1:
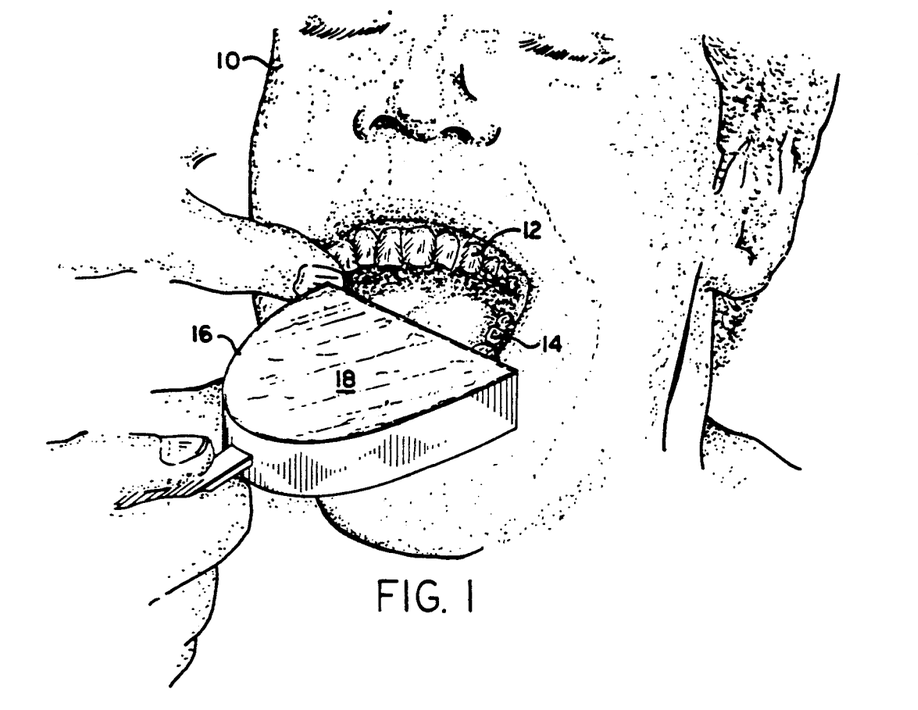
FIG. 1 illustrates taking an arch impression using an impression tray and impression material.
Figure 11:
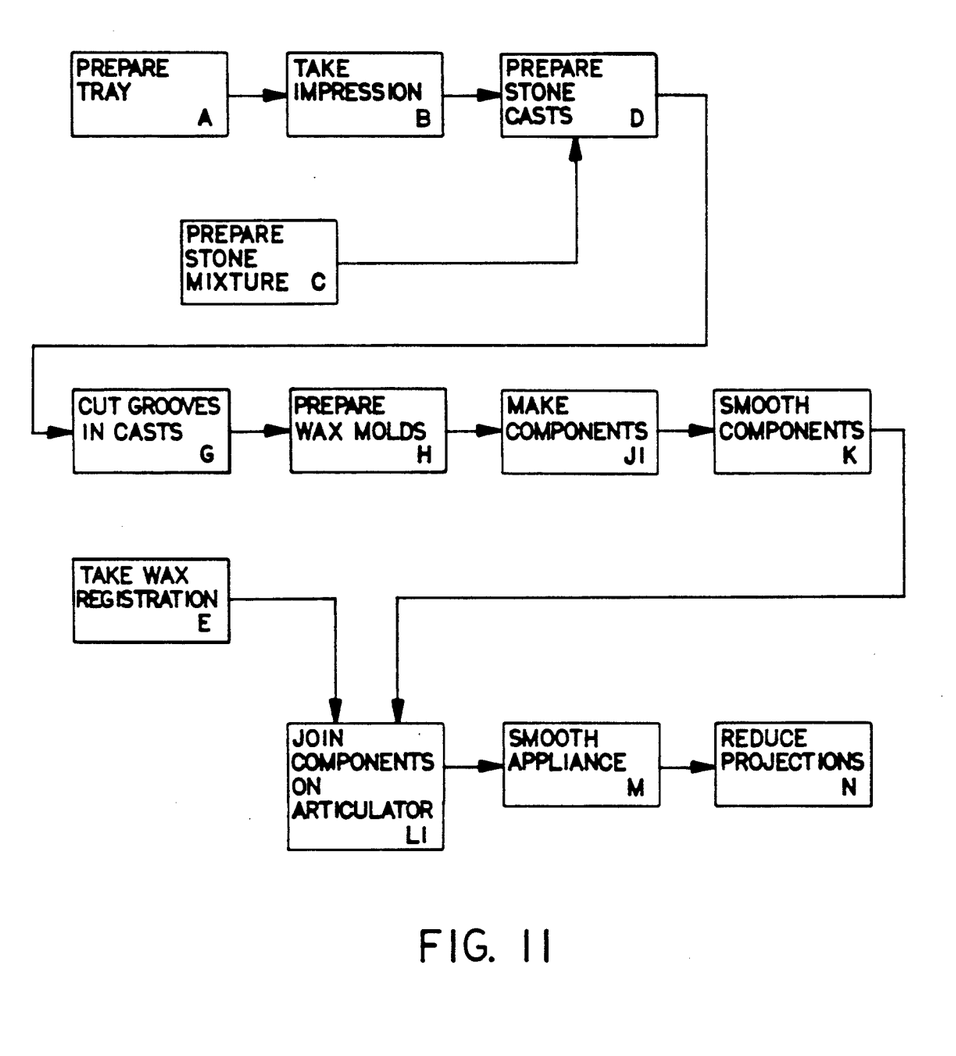
FIG. 11 is a block diagram of the first method of manufacture.

The steps required for a first method of manufacture are shown in block diagram form in FIG. 11 and the description follows. FIG. 1 shows patient 10, having an upper dental arch 12 and a lower dental arch 14, with an impression being taken of the upper dental arch using impression tray 16. In taking this impression, impression tray 16 is first filled with an impression material 18, which is typically a gel formed by mixing a powder, such as alginate, with water. The step of preparing impression tray 16 is indicated by block A and the step of taking the impression is indicated by block B of FIG. 11. In taking the impression, impression tray 16 is placed in the mouth and seated over one of the dental arches. After impression material 18 has set impression tray 16 is then removed from the upper arch of teeth 14, which results in a recess in the impression tray with the same shape as the exterior of the upper arch of teeth 12.

Figure 2:
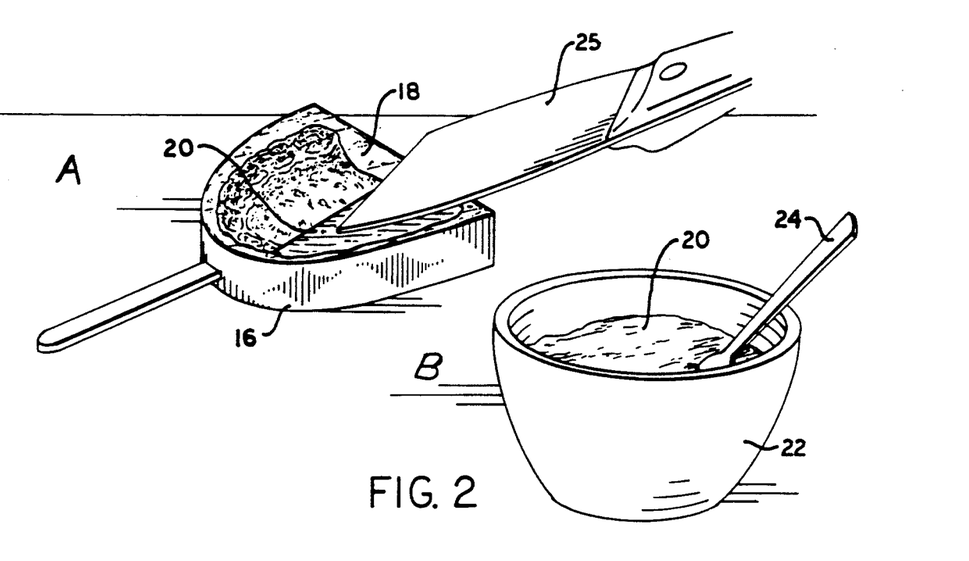
FIG. 2A illustrates making a stone cast from the arch impression.
FIG. 2B illustrates preparing stone material.

A dental stone mixture 20 is then made, as shown in FIG. 2B and indicated by Block C in FIG. 11, by mixing stone powder and water in mixing bowl 22 using a spoon 24. Stone mixture 20 is then loaded into the recess in impression tray 16 using a spatula 25, while the tray is vibrated to insure that the material has entered all of the recesses in the impression, as shown in FIG. 2A and indicated by block D of G FIG. 11. After stone mixture 20 has hardened it is then removed as upper stone cast 26. This same procedure is also repeated for the lower dental arch 14 to obtain a lower stone cast 28, with both completed casts being shown in FIG. 4.

Figure 3:
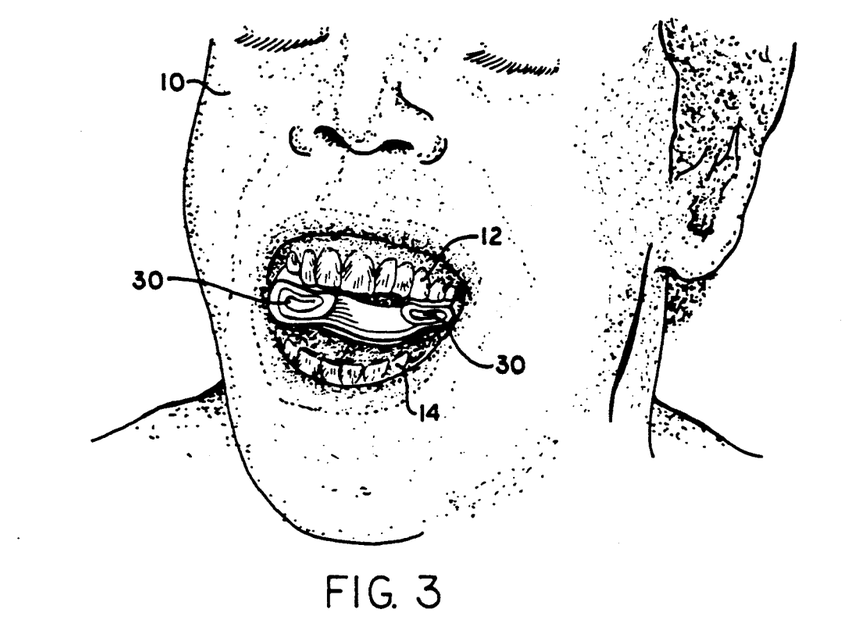
FIG. 3 illustrates taking a wax bite registration.

As shown in FIG. 3, a wax bite registration 30 is taken. In this process a sheet of wax is folded into the pattern, as shown in the figure, after the wax is heated to a temperature adequate to soften the wax but not high enough to burn the patient's mouth. In taking wax bite registration 30, patient 10 is required to protrude the mandible between 60 and 75 percent of its maximum ability to protrude. The mouth must also be opened between 10 and 15 degrees, with a spacing of approximately 5 to 8 mm. between the incisal edges of the front teeth. These requirements are monitored and established by the dentist who instructs the patient while the registration is being taken. A measuring gauge, such as a George Gauge, can also be used to accurately determine the amount of protrusion of the mandible.

After wax bite registrations 30 are taken they are then removed from the mouth and allowed to cool until solid. After cooling wax registrations 30 can be reinserted between the upper dental arch 12 and the lower dental arch 14 to check for comfort in this jaw position, and then if necessary the entire process is repeated until the patient is comfortable with the jaw in this position. This entire process is included in the process of taking wax bite registration 30 as indicated by block E of FIG. 11.

Figure 4:
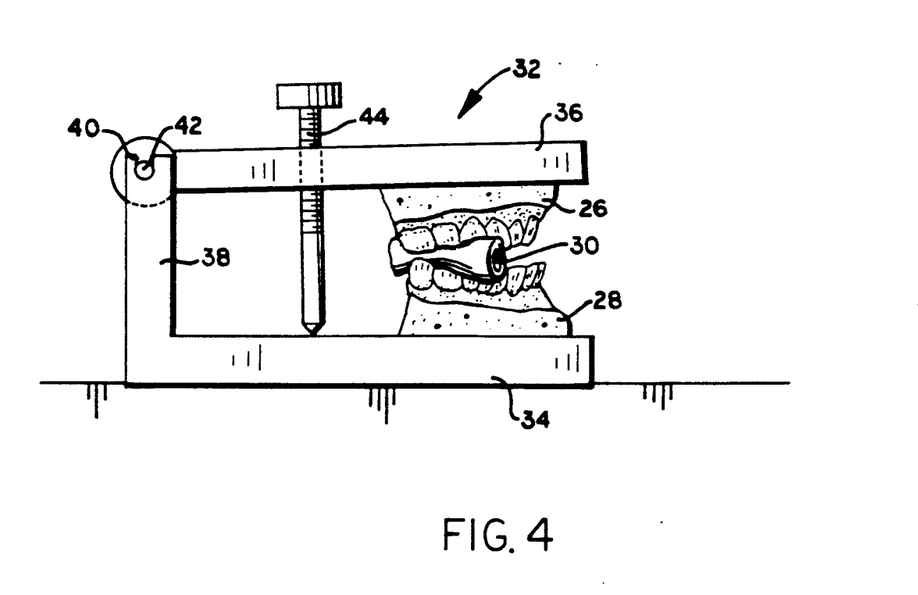
FIG. 4 illustrates positioning the casts using the wax registration and the dental articulator.

A dental articulator 32, shown in FIG. 4, is used to reproduce the same relationship of upper stone cast 26 to lower stone cast 28 as that of the upper dental arch 12 and the lower dental arch 14 established by wax bite registration 30.

Dental articulator 32 consists of a planar lower bow 34, an opposed upper planar surface, upper bow 36, two vertical supports 38, each having upwardly directed opposed and aligned grooves 40 which receive outwardly projecting aligned and opposed pins 42 extending outwardly from the upper bow. Pins 42 provide a hinge axis to permit upper bow 36 to pivot with respect to lower bow 34 and change the angle between the two. A threaded adjustable guide pin 44 is threaded into a mating threaded hole in upper bow 36 to provide a means for setting the angle between upper bow 36 and lower bow 34.

Upper stone cast 26 is mounted on upper bow 36 and lower stone cast 28 is mounted on lower bow 34 such that dental articulator 32 will hold the two casts in the same relationship that upper dental arch 12 and lower dental arch 14 had when wax bite registration 30 was taken.

Figure 5:
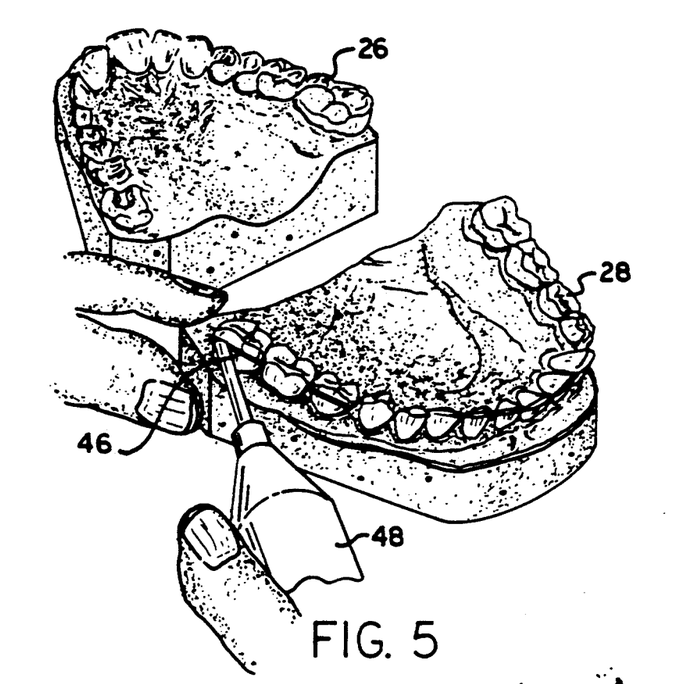
FIG. 5 illustrates cutting grooves into teeth in the upper dental cast using a handpiece and bur.

As shown in FIG. 5 and indicated by block G of FIG. 11, prior to mounting stone casts 26 and 28 on dental articulator 32, grooves 46 are cut into buccal surfaces of two of the back teeth using a conventional handpiece 48 mounting a small round bur. Grooves 46 are cut parallel to the occlusal surfaces of the teeth just below the height of contour adjacent to the gum line. Since this is the best area for retention, as described earlier, this provides the best place to locate the attachment means.

Figure 6:
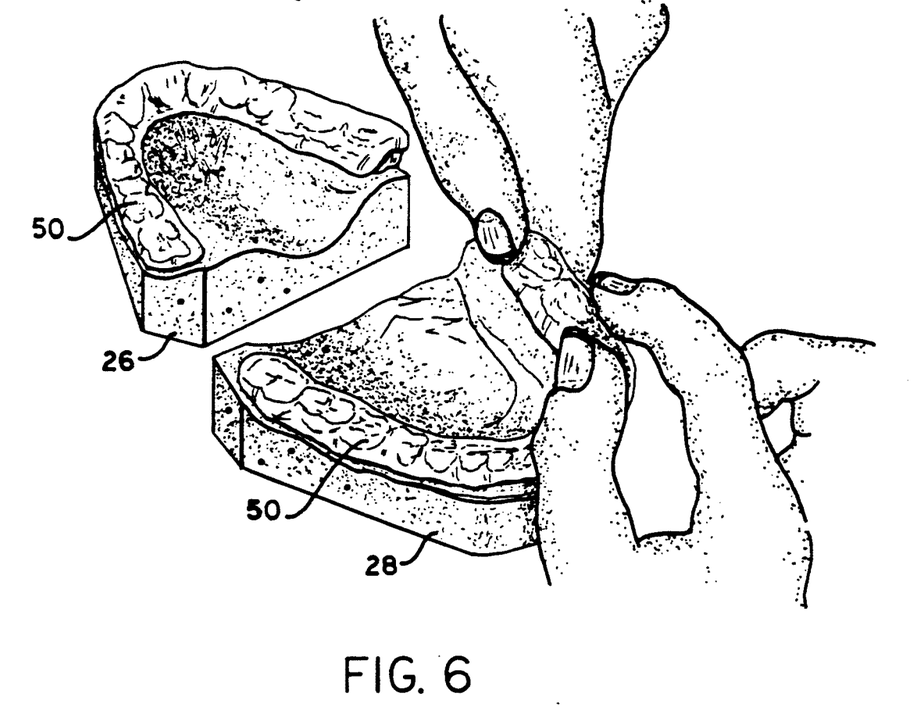
FIG. 6 illustrates molding wax around the upper and lower casts after grooves have been cut into the teeth.

As shown in FIG. 6, wax molds 50 are then made by forming heated softened wax sheets by hand over both upper and lower stone casts 26 and 28 to near the gum line. On the maxillary arch, the wax runs across the palate and extends posteriorally almost to the soft palate. The wax will cover the teeth and extend to an area near the gumline. On the mandibular cast, the wax will extend over the lingual surfaces of the teeth and approximately 5 mm. onto the soft tissues. The wax will also extend over the teeth to an area near the gumline. The wax is molded and pressed to place, particularly in grooves 46 on the buccal surfaces of the two posterior molars containing the grooves, in order to adapt it well to register the attachment projections. After wax molds 50 cool they are removed from the upper and lower stone casts 26 and 28. This entire process is indicated by block H of FIG. 11.

An upper plastic component 52 is then made from the wax mold 30 of upper stone cast 26 and a lower plastic component 54 is made from the wax mold of lower stone cast 28. These resulting parts, made of plastic preferrably of Bruxeze, have inner surfaces identical to the respective outer surfaces of the wax molds which are obtained by conventional laboratory dental techniques for replicating such parts, such as the lost wax technique. This entire process is indicated by block J1 of FIG. 11.

Components 52 and 54 are then smoothed and polished using a handpiece and appropriate accessories, as indicated by block K of FIG. 11.

As described earlier, these plastic replicas, upper component 52 and lower component 54, each have a projection directed inwardly from the buccal side of two rear teeth resulting from grooves 40 which were cut into the teeth replicas respectively in stone casts 26 and 28. If Bruxeze plastic material is used for these parts, it will soften slightly at body temperature and eliminate pressure points. This will eliminate the necessity for a liner.

Cast 26 and cast 28 are then mounted upon dental articulator 32 in any order. This is shown in FIG. 4. The easiest approach is to mount lower stone cast 28 first, however the procedure would essentially the same if upper stone cast 26 were mounted first. Wet dental plaster is mixed and prepared, and placed across the face of the lower stone cast 28 to be attached to lower bow 34. Cast 28 is then placed on bow 34 as shown and the dental plaster allowed to set. After the dental plaster on lower cast 28 has set, wax bite registration 30 is then placed against the lower stone cast as shown. Upper stone cast 26 is then placed into wax bite registration 30 to accurately position it relative to the opposing lower stone cast 28. Wet dental plaster is then placed on upper stone cast 26 and similarly used to attach this cast to upper bow 36. At this time the adjustable guide pin 44 is also adjusted such that the angle between upper bow 36 and lower bow 34 is determined such that the two casts and wax bite registration 30 are properly related. After the dental plaster of upper stone cast 26 hardens, wax bite registration 30 is removed and the relationship on upper stone cast 26 and lower cast 28 measured and confirmed to be correct using the same criteria as that used when wax bite registration 30 was taken. The relationship established in this manner between stone casts 26 and 28 is the same as the dental arches had when wax bite registration 30 was taken. This process is a part of attaching the components together on articulator 32 indicated by block L1 of FIG. 11.

In this attachment process flat disk shaped rings are usually attached to the articulator bows before the casts are attached to permit a later removal of the casts and subsequent use of the articulator. This use of rings has no bearing on the method of manufacturing as described here however, and since this use can either be included or omitted with the same final results it is not described further.

Figure 7:
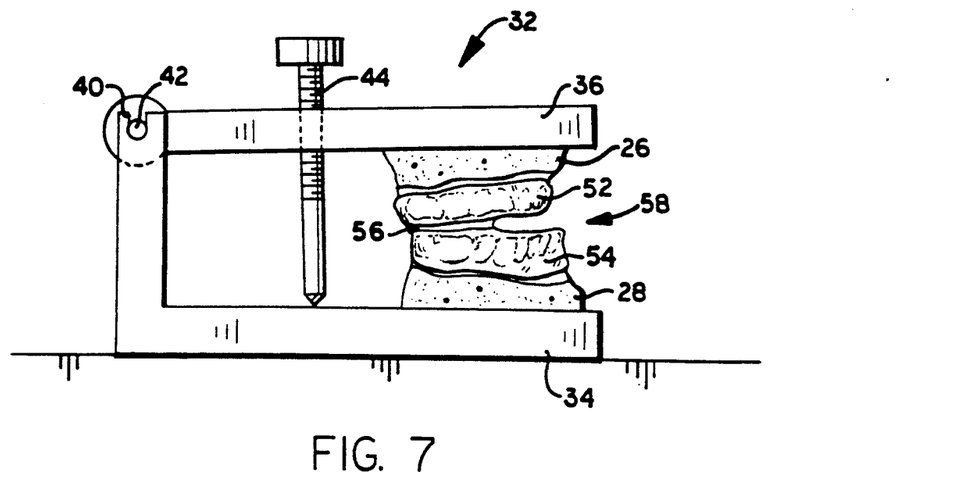
FIG. 7 illustrates securing the upper and lower plastic parts of the appliance together while being held in the relationship established by the wax registration on the dental articulator.

As shown in FIG. 7, upper plastic part 52 and lower plastic part 54 are then placed over their respective stone casts 26 and 28. Since articulator 32 has been adjusted and stone casts 26 and 28 have been mounted using wax bite registrations 30, plastic parts 52 and 54 are held in the same relationship they would have had if mounted over upper dental arches 12 and 14 when the wax bite registration was taken.

An adhesive 56 is then placed on upper component 52 and lower component 54 on the portions adjacent to their posterior quadrants from the first bicuspid through the second or third molar area, leaving a rectangular opening in the anterior portion of the appliance to allow proper air flow when the appliance is placed in the mouth. The bonding procedure involves placement of the resin over the occlusal surfaces of that posterior segment flowing slightly onto the back portions. Adhesive 56 is allowed to cure and the completed appliance 58 is then removed from stone casts 26 and 28. The preferred adhesive here is an acrylic resin of two parts, a liquid and a powder. When these two parts are mixed together a polymerization process forms a solid acrylic plastic material. This particular adhesive is not critical however, since a number of other polymerizing plastics or even thermo-plastic materials when heated to plasticity could be used to produce an identical result. This complete process from placing components 52 and 54 over their respective stone casts 26 and 28 and joining the components together is indicated by block L1 of FIG. 11.

Completed appliance 58 is then smoothed and polished using a handpiece and appropriate accessories, which is indicated by block M of FIG. 11.

Figure 8:
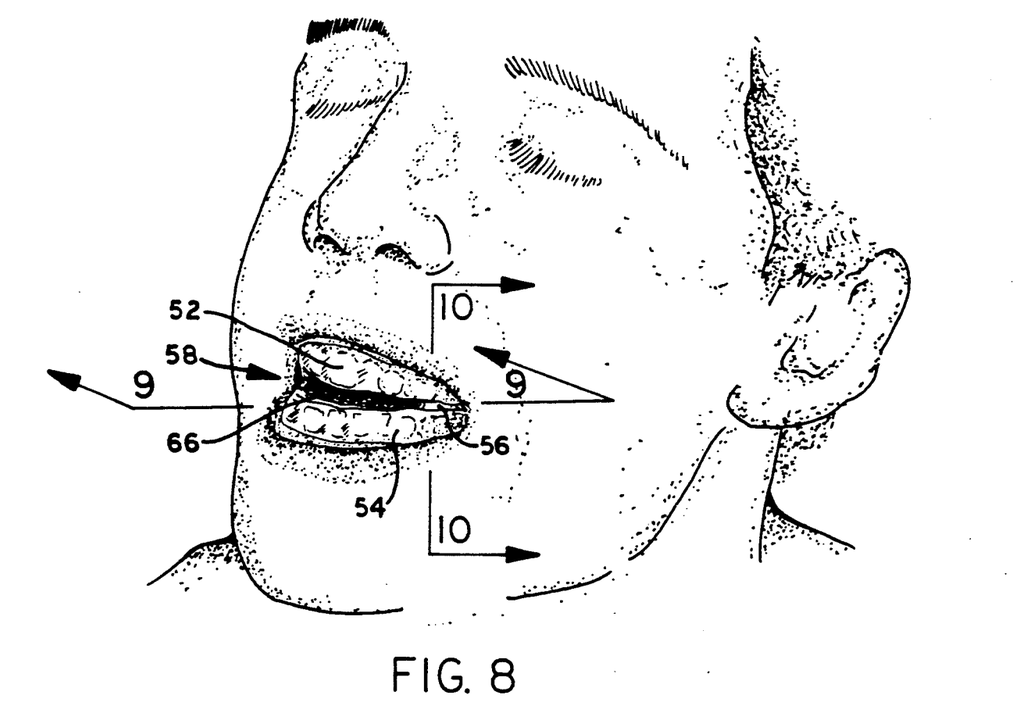
FIG. 8 illustrates the appliance secured within the mouth with the jaw being held in the necessary relationship to prevent sleep apnea.
Figure 9:
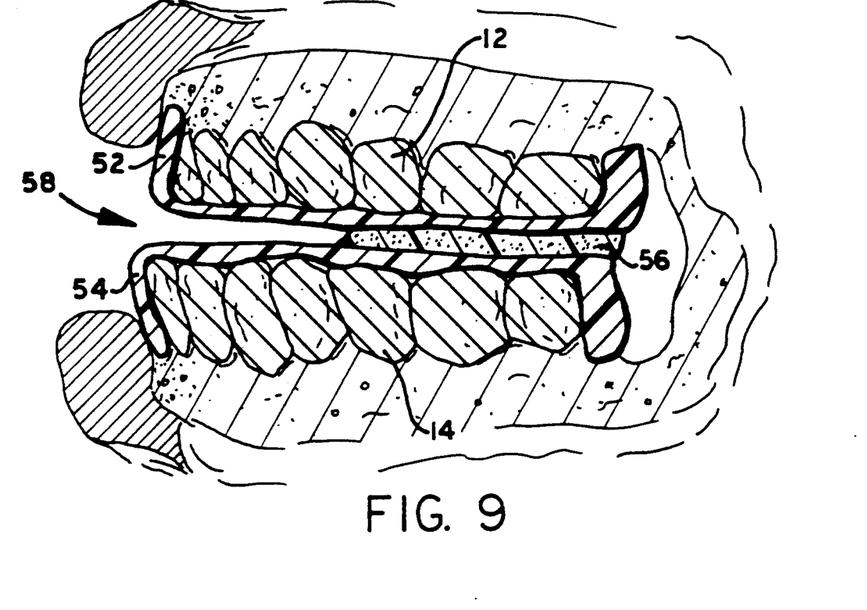
FIG. 9 is a cross-section of the appliance, taken along 9—9 in FIG. 8, showing its relationship to the dental arches.

Appliance 58 is then mounted over the patient's teeth, as shown in FIGS. 8 and 9. Appliance 58 will hold the teeth in the relationship previously established by wax bite registration 30. Central opening 66 is the opening provided for breathing.

Figure 10:
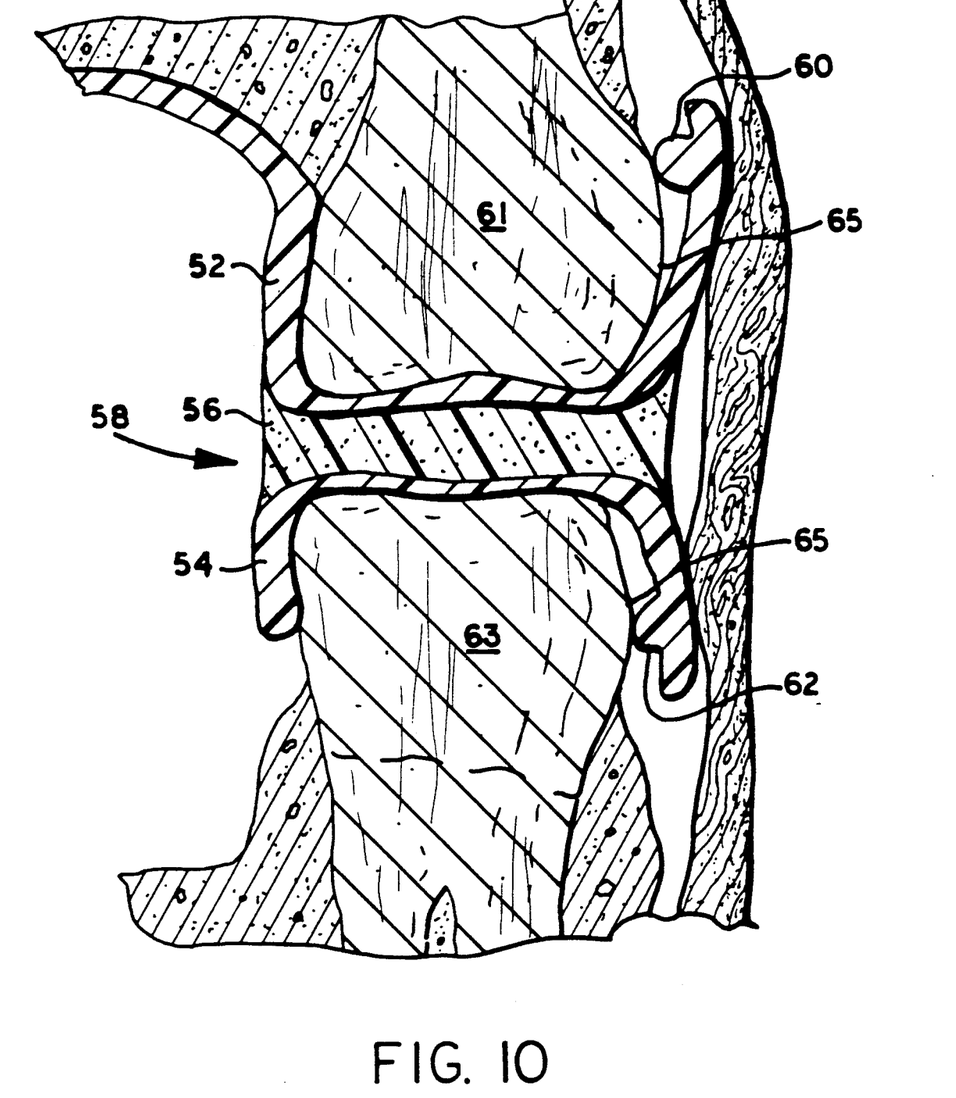
FIG. 10 is a detail of a cross-section of a section of the appliance, taken along 10—10 in FIG. 8, showing projections engaging a single tooth.

A cross-section detail of a portion of appliance 58 in FIG. 10, shows projection 60 extending from upper component 52 inward against tooth 61 and projection 62 extending from lower component 54 inward against tooth 63 holding the appliance in place. Note that the height of contour 65 of each tooth lies occlusal to both projections 60 and 62 so that the walls of the appliance must be flexed outward in order to place or remove the appliance which provides the gripping force. In this figure projections 60 and 62 are exaggerated to better illustrate the attachment means. In an actual application, the projections would not flex the sides of the appliance outward nearly as much as would be required here.

If appliance 58 is attached too tightly the attachment force can be reduced by grinding off some of the extensions, which includes extensions 60 and 62 of components 52 and 54, as well as the extensions on the opposite sides, using a conventional handpiece and bur. This process is indicated by block N of FIG. 11. As described earlier this would be done in a number of steps, with each step being a small reduction in the extensions followed by trying the appliance in the patient's mouth, until the desired grip consistent with comfort is obtained. It is anticipated that this step will be unnecessary with experience in manufacturing this appliance.

Figure 12:
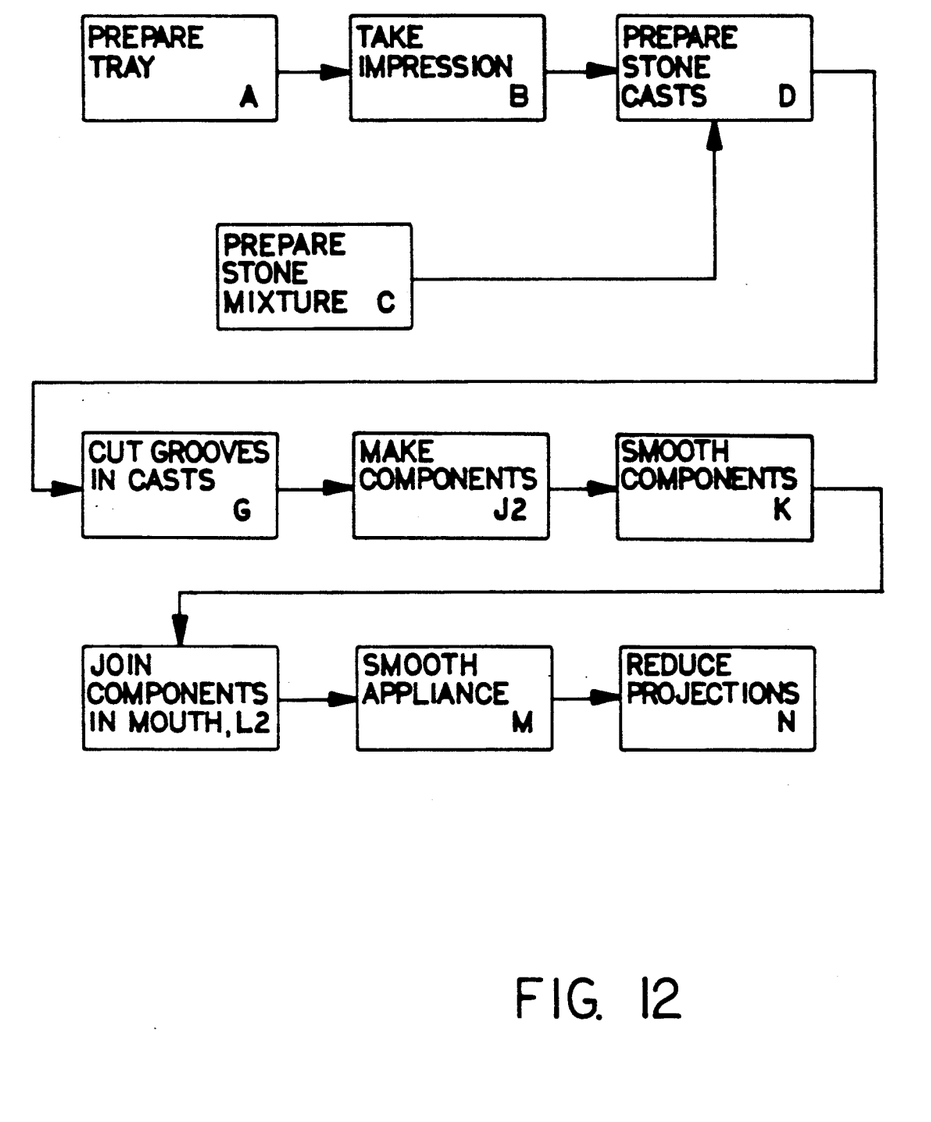
FIG. 12 is a block diagram of the second method of manufacture.

The steps required for the second method of manufacture are shown in block diagram form in FIG. 12. Here, the steps indicated by blocks A, B, C, D and G are identical with the first method resulting in stone casts 26 and 28. Here however block J2, which now follows block G, indicates making components 52 and 54 out of plastic by molding a sheet of plastic directly over the respective stone cast and then allowing it to harden.

This can be done using a number of materials and processes. Molding a sheet of unpolymerized two-part plastic over the casts and allowing the plastic to polymerize before removal is one process. Using a sheet of unpolymerized light polymerizing plastic can also be molded over the casts and an appropriate light source used. A sheet of thermoplastic material, heated to a temperature which would permit molding it around the cast and allowing it to cool before removal, could also be used.

The plastic components prepared in this manner are arranged to have the same dimensions and cover the same portions of the respective cast as wax molds 50 of block H in FIG. 11. The components 52 and 54 are then smoothed and polished as before, as indicated by block K of FIG. 12.

Figure 8A:
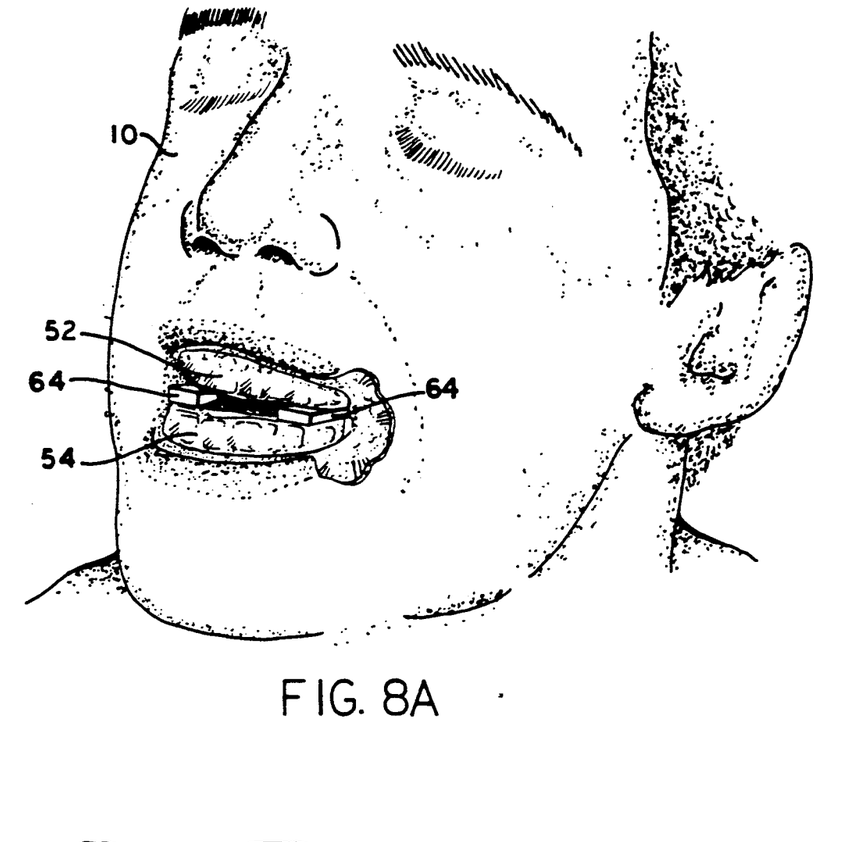
FIG. 8A illustrates securing the upper and lower appliances together in the mouth using the second method.

In the next step components 52 and 54 are first mounted over the respective upper and lower arch of teeth 12 and 14 as shown in FIG. 8A. A wedge shape of plastic material 64 is used to attach component 52 to 54. Plastic material 64 is sized such that the same relationship between components 52 and 54 as was obtained in the first method with wax bite impression 30 can be obtained here. Here also, plastic material 64 can be a two part epoxy which is mixed, sized and positioned between the components and allowed to harden, a wedge shape of plastic of the proper size which is attached to the components using a two part resin, or any equivalent attachment means.

During the attachment of component 52 to component 54, the position requirements described earlier for this application are monitored and established by the dentist as before while the components are being attached to each other. This results in the relationship between the upper and lower arch of teeth 12 and 14 while component 52 is attached to component 54 being made the same as in the first method when the wax bite registration was taken, and therefore the relationship between these components will also be the same. This process of joining component 52 to 54 in this manner is indicated by block L2 of FIG. 12.

After being joined, components 52 and 54 are smoothed and, if necessary, reduced in the same way as in blocks M and N of FIG. 11, here also indicated by equivalent blocks M, and N of FIG. 12.

The simplicity of this second method is obtained at the expense of accuracy. The more accurate first method using a wax bite registration and a dental articulator will probably be used most for permanent appliances, while the less accurate second method omitting these steps, which can be accomplished in the dentist's office, will probably be used the most for temporary appliances.

As discussed earlier, the simple attachment means obtained in both of these methods, resulting in inwardly directed projections as a part of the appliance itself, can be used with any dental appliances in which the appliance must be securely retained to the teeth with patient comfort still being maintained, orthodontic, orthopedic, or otherwise. The only requirement is that these other appliances must require the same or a lesser attachment force.

The fact that these projections are a part of the appliance itself results in an easy to construct, easy to clean, and strong appliance, which can readily be adjusted to obtain a comfortable fit.

If the preferred plastic material of Bruxeze, which softens slightly at body temperature, is used for the components then the use of a liner will not be required to eliminate pressure points. This will also make cleaning the appliance easier. If another plastic is used however, the two methods of manufacture will remain the same. If the plastic used requires more force to deform it, then the projections would then have to be reduced to a smaller dimension and the fitting process could be more critical. In all other respects however the manufacturing methods would remain the same.

The essential element of this invention is the manufacture of an appliance which grips the teeth using a projection from the appliance itself. If an appliance attached to only one arch were required, such as a mouthguard for athletes, in both methods the steps having to do with preparing two components and the joining of one component to another are merely omitted as described below.

In the first method the wax bite registration of block E and mounting and aligning casts on the articulator of Block F in FIG. 11 would be omitted. In all of the other blocks only one part would be prepared. In the second method joining the components together in the mouth of Block L2 in FIG. 12 would be omitted. In all of the other blocks only one part would be prepared.

With these deletions and changes, the two methods apply to appliances having only one component.

While this invention has been described with reference to an illustrative embodiment, this description is not intended to be construed in a limiting sense. Various modifications of the illustrative embodiment, as well as other embodiments of the invention, will be apparent to persons skilled in the art upon reference to this description. It is therefore contemplated that the appended claims will cover any such modifications or embodiments as fall within the true scope of the invention.

I claim:

1. A method of manufacturing a dental appliance comprising the steps of:

a) preparing impression material, loading an impression tray with the prepared impression material, taking an impression of a first dental arch using the impression tray, allowing the impression material to cure, removing the impression tray from the dental arch; and b) preparing a stone mixture, filling the impression of the first dental arch in the impression tray with the stone mixture, allowing the mixture to harden, removing the resulting cast from the impression; and c) cutting grooves in the teeth replicas in the cast of the first dental arch, the grooves being oriented essentially parallel to the occlusal surfaces and positioned between the gum tissue replica and the height of contour of the tooth replica, having at least one groove on the buccal side of at least two posterior teeth, the teeth being located on opposite sides of the dental arch, and d) using said cast of the first dental arch as a form in making a plastic first component for the first dental arch, which will fit and cover the teeth extending to near the gumline; and e) smoothing and polishing said first component.

2. The method of claim 1 further comprising successively trying said component over the matching dental arch to determine the fit, removing the component from said dental arch, and reducing the projections extending from the component resulting from the grooves cut in the cast to obtain a desired fit.

3. The method of manufacturing a dental appliance of claim 1 further comprising:

a) preparing impression material, loading an impression tray with the prepared impression material, taking an impression of the opposite second dental arch using the impression tray, allowing the impression material to cure, removing the impression tray from the dental arch; and b) preparing a stone mixture, filling the impression of the second dental arch in the impression tray with the stone mixture, allowing the mixture to harden, removing the resulting cast of the second dental arch from the impression; and c) cutting grooves in the teeth replicas in the cast of the second dental arch, the grooves being oriented essentially parallel to the occlusal surfaces and positioned between the gum tissue replica and the height of contour of the tooth replica, having at least one groove on the buccal side of at least two posterior teeth, the teeth being located on opposite sides of the dental arch, and d) using said cast of the second dental arch as a form in making a plastic second component for the second dental arch, which will fit and cover the teeth extending to near the gumline; and e) smoothing and polishing said second component; and f) assembling an appliance from the first and second components by joining said components together using an acrylic adhesive, and allowing said adhesive to cure while holding said components in a predetermined position with respect to each other.

4. The method of claim 3 further comprising successively trying said appliance over the matching dental arches to determine the fit, removing the appliance from the dental arches; and reducing the projections extending from the first and second components, resulting from the grooves cut in the cast, until a desired fit is obtained.

5. The method of manufacturing a dental appliance of claim 3 whereby assembling an appliance from the first and second components comprises:

a) placing said first and second components in the mouth over their respective mating dental arches, and b) placing a predetermined size and shaped plastic wedge between said first and second components and at the end of the arches opposite the mouth, the wedge being sized and shaped such that with the wedge between the components the jaw can be placed in said predetermined position; and c) placing said jaw in said predetermined position; and d) placing an acrylic adhesive between said first and second components and the wedge; and e) allowing the adhesive to cure while said jaw is being held in said predetermined position.

6. The method of manufacture is in claim 3 using Bruxeze as the plastic for the second component.

7. The method of manufacturing a dental appliance of claim 1 whereby the impression of the first dental arch is of the upper dental arch, and whereby using the cast made from said impression of the first dental arch in making a plastic first component comprises:

a) making a wax mold by covering said cast of the first dental arch with a sheet of wax softened by heat such that the wax sheet extends over the cast of the first dental arch and covers the palate replica posteriorly to near the soft palate, and covers the teeth replicas to near the gumline, the wax being particularly pressed to place in the grooves on the buccal surfaces of the posterior molars in order to register the grooves, and b) allowing the wax to harden and removing the wax mold of the first dental arch from said cast of the first dental arch, and c) making a plastic first component from the wax mold of the first dental arch using the lost wax technique, smoothing and polishing said first component; and d) preparing impression material, loading an impression tray with the prepared impression material, taking an impression of the opposite lower second dental arch using the impression tray, allowing the impression material to cure, removing the impression tray from the dental arch; and e) preparing a stone mixture, filling the impression of the second dental arch in the impression tray with the stone mixture, allowing the mixture to harden, removing the resulting cast of the second dental arch from the impression; and c) cutting grooves in the cast of the second dental arch in the teeth replicas, the grooves being oriented essentially parallel to the occlusal surfaces of the said teeth and positioned between the gum tissue replica and the height of contour of said teeth, such that at least one groove is cut on the buccal side of at least two posterior teeth, the two teeth being located on opposite sides of the dental arch, and d) making a plastic second component from the cast of the lower dental arch comprising:

i) making a wax mold by covering the cast of the lower dental arch with a sheet of wax softened by heat and sized such that the sheet of wax will extend over the replicas of the lingual surfaces of the teeth a short distance onto the soft tissues and extend over the teeth to an area near the gumline, the wax being particularly pressed to place in the grooves on the buccal surfaces of the posterior molars in order to register the grooves, allowing the wax to harden, removing the wax mold from the cast; and ii) making a plastic replica of the mold using the lost wax technique; and iii) smoothing and polishing said second component; and e) taking a wax bite registration of the upper and lower archs while the jaw is being held in said predetermined position; and g) mounting the cast of the upper dental arch on the upper bow of an articulator and mounting the cast of the lower dental arch on the lower bow of said articulator using the wax bite impression to place the casts and adjust the articulator such that the casts have the same relationship as the upper and lower arches did when the wax bite impression was being taken, removing the wax bite registration from the articulator, and h) placing the first and second components over the respective mating upper and lower casts on the articulator, placing the casts in the same relationship as that previously determined by the wax bite impression, joining the components together using an acrylic adhesive by placing the adhesive on the upper component and lower component on those portions adjacent to the posterior quadrants from the first bicuspid at least through the second molar area, leaving an opening in the anterior portion of the appliance, allowing the adhesive to cure and removing the assembled appliance from the casts.

8. The method of manufacture as in claim 7 further comprising successively trying said appliance over the matching dental arches to determine the fit, removing the appliance from the dental arches, and reducing the projections extending from the upper and lower components resulting from the grooves cut in the casts to obtain a desired fit.

9. The method of manufacture as in claim 7 using Bruxeze as the plastic for the first and second component.

10. The method of manufacture as in claim 1 using Bruxeze as the plastic for the first component.

* * * * *